United States Patent [19]
Werp et al.

[11] Patent Number: 5,931,818
[45] Date of Patent: Aug. 3, 1999

[54] METHOD OF AND APPARATUS FOR INTRAPARENCHYMAL POSITIONING OF MEDICAL DEVICES

[75] Inventors: Peter R. Werp, Los Gatos, Calif.; Rogers C. Ritter, Charlottesville, Va.; Walter M. Blume, Webster Groves, Mo.

[73] Assignee: Stereotaxis, Inc., St. Louis, Mo.

[21] Appl. No.: 08/969,165

[22] Filed: Nov. 12, 1997

Related U.S. Application Data

[63] Continuation-in-part of application No. 08/920,446, Aug. 29, 1997.

[51] Int. Cl.⁶ .................................................. A61M 31/00
[52] U.S. Cl. ......................... 604/270; 604/164; 600/434
[58] Field of Search .............................. 604/95, 164, 170, 604/270; 128/899; 600/434; 606/108

[56] References Cited

U.S. PATENT DOCUMENTS

| | | |
|---|---|---|
| 4,244,362 | 1/1981 | Anderson . |
| 5,425,382 | 6/1995 | Golden et al. . |
| 5,431,460 | 7/1995 | Gabriel ..................................... 604/270 |
| 5,622,169 | 4/1997 | Golden et al. . |
| 5,624,430 | 4/1997 | Eton et al. . |

*Primary Examiner*—Michael Buiz
*Assistant Examiner*—Julian W. Woo
*Attorney, Agent, or Firm*—Howell & Haferkamp, L.C.

[57] ABSTRACT

A catheter and magnet combination adapted for intraparenchymal positioning of the catheter in the body with a magnetic field. The catheter has a proximal and distal ends and a lumen therebetween. A magnet is disposed in the distal end of the lumen so that the distal end of the catheter can be positioned within the body with the aid of an externally applied magnetic field. A tether is attached to the magnet and extends through the lumen and out the proximal end so that the magnet can be removed from the catheter through the lumen once the distal end of the catheter is properly positioned. In one embodiment of the invention, the tether is sufficiently stiff to be able to push the catheter through the tissue. With this embodiment, the magnetic field orients the magnet and thus the tip of the catheter, and some or all of the force for moving the catheter is applied via the tether.

18 Claims, 3 Drawing Sheets

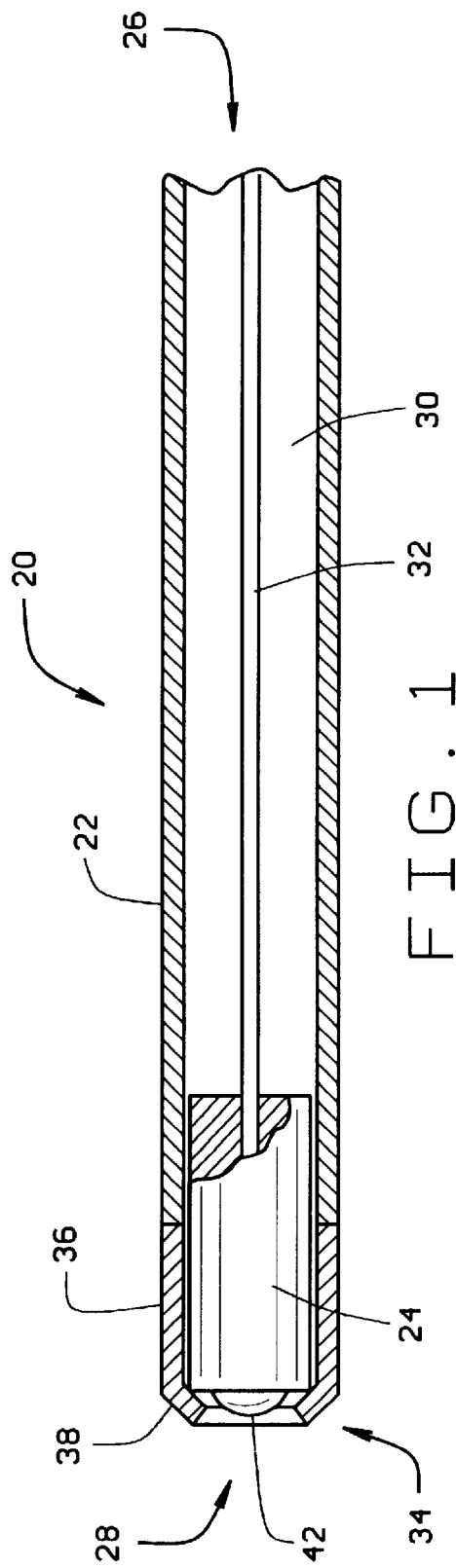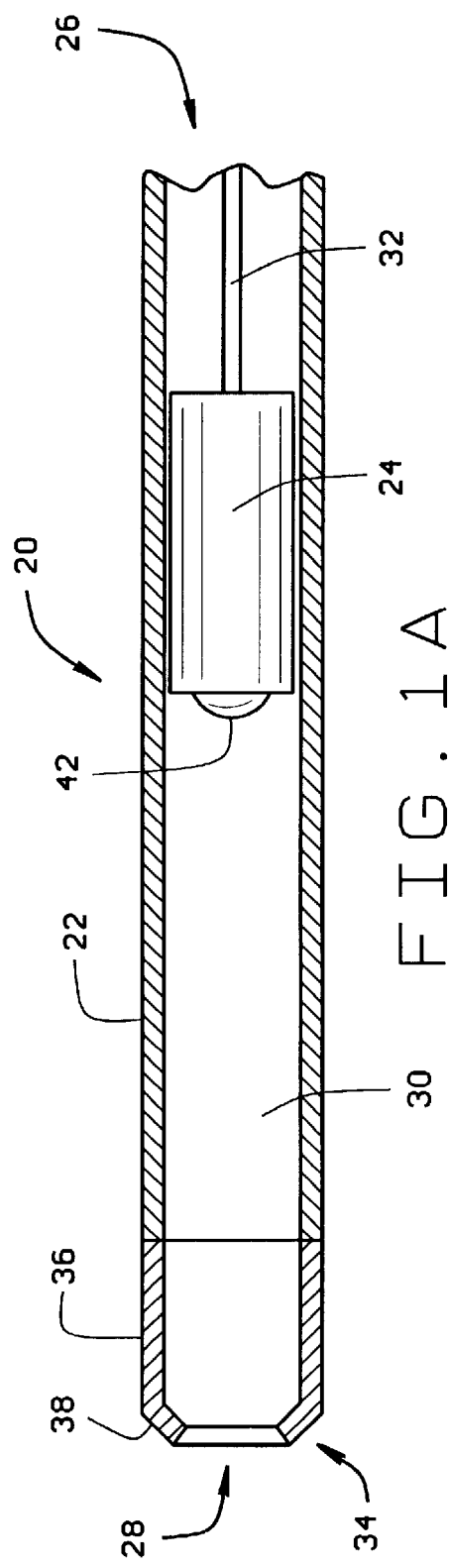

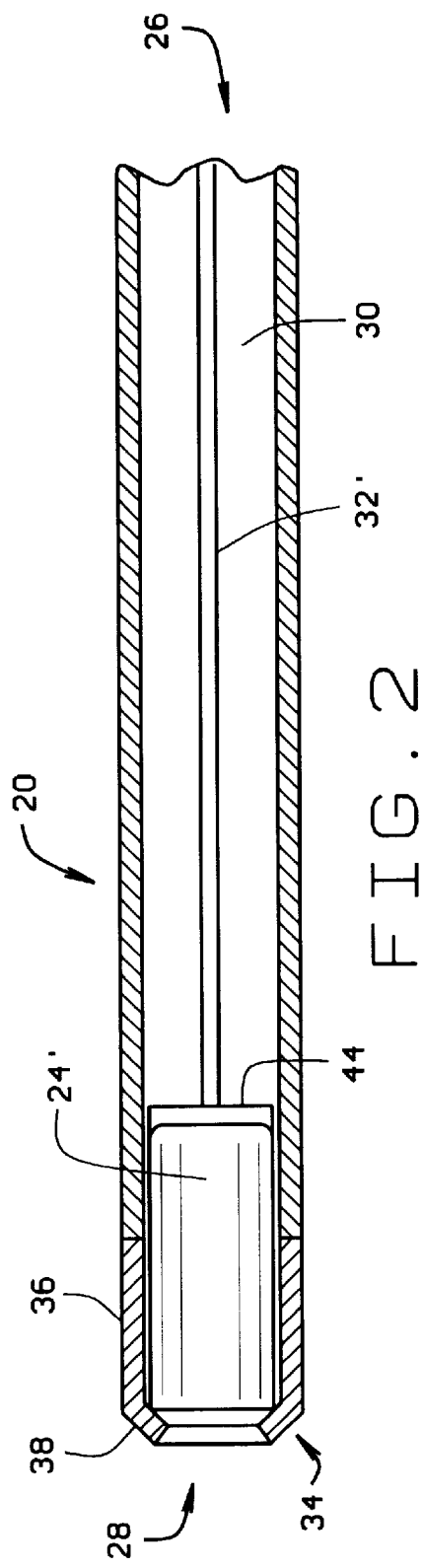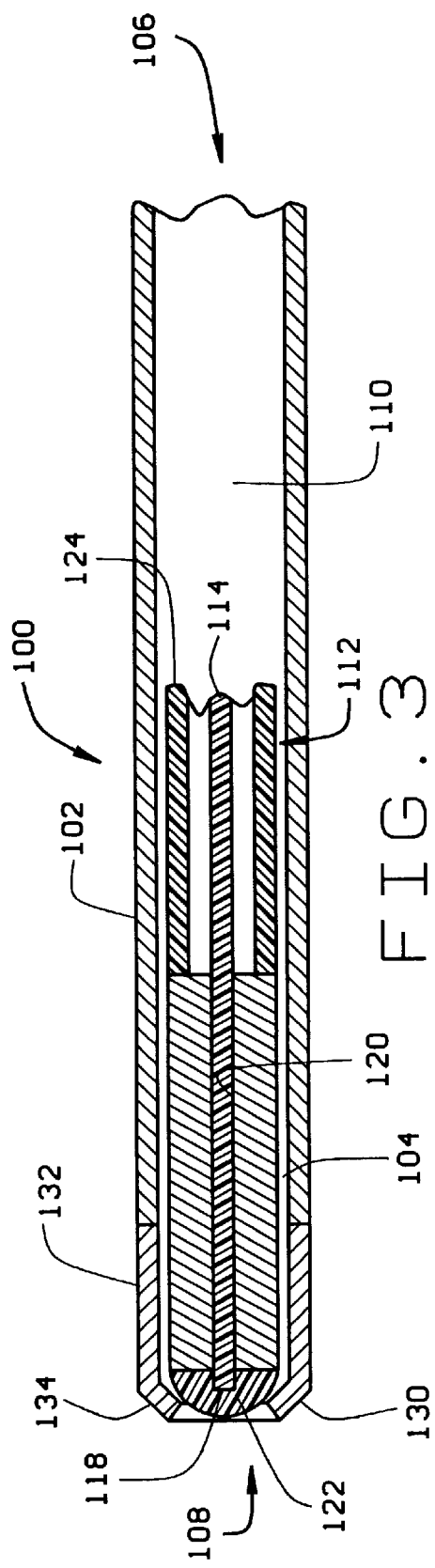

METHOD OF AND APPARATUS FOR INTRAPARENCHYMAL POSITIONING OF MEDICAL DEVICES

CROSS REFERENCE TO RELATED APPLICATION

This application is a continuation in part of U.S. patent application Ser. No. 08/920,446, entitled Method for Magnetically controlling Motion Direction of a mechanically pushed catheter, filed Aug. 29, 1997, incorporated herein by reference.

FIELD OF THE INVENTION

This invention relates to a method of, and apparatus for positioning a medical device in the body through the tissue (intraparenchymally).

BACKGROUND OF THE INVENTION

Many diagnostic and therapeutic medical procedures require transporting a medical device through the body to a particular location. There are two principal routes through the body: through the body tissue (intraparenchymally) or through the blood vessels (intravascularly).

Several methods and apparatus have been developed for the intraparenchymal placement of medical devices in the body. One such method and apparatus, disclosed in Howard et al., U.S. Pat. No. 5,125,888, incorporated herein by reference, employs a magnet releasably attached to the medical device. The device is moved within the body by the controlled application of a magnetic field to the magnet. The magnetic field guides the magnet, which in turn guides the medical device to which it is attached. Once the medical device is in its desired position the magnet is released from the medical device and recovered, typically by manipulating it out of the body with a magnetic field.

While prior methods and apparatus which employed magnetism to position medical devices have numerous advantages, they also had some draw backs. First, recovery of the magnet could be difficult and time consuming, prolonging the medical procedure. Second, in some instances it can be difficult to generate a magnetic field sufficiently strong to move the medical device through the tissue, and in a desired strength and direction to move the medical device along the desired path.

SUMMARY OF THE INVENTION

The method and apparatus of the present invention involve magnetically guiding a medical device on an intraparenchymal path through the body. Generally according to the method of this invention a magnet is provided in the lumen of a catheter, adjacent the distal end with a tether extending from the magnet, through the lumen of the catheter to the proximal end. The distal end of the catheter has a restriction to retain the magnet in the lumen. The distal end of the catheter can be guided intraparenchymally to its desired position by the controlled application of a magnetic field, which acts on the magnet inside the lumen. Once the distal end of the catheter is in its desired position, the magnet can be quickly and easily withdrawn through the lumen of the catheter with the tether, eliminating the need to detach and manipulate the magnet out of the body encountered with some prior art methods.

Further, according to one embodiment of the invention, the tether can be sufficiently stiff to function as a guide wire to help advance the catheter through the tissue. In this embodiment, the magnetic field need only be sufficiently strong to freely orient the magnet inside the distal tip of the catheter, and the motive force for advancing the catheter through the tissue is provided by tether or guide wire. The distal end of the tether/guide wire is preferably relatively flexible to allow the magnet to freely orient the distal end of the catheter under the influence of an applied magnetic field. The proximal end of the tether/guide wire is preferably relatively stiff so that it can urge the distal end of the catheter through the tissue.

The method and the catheter/guide wire or catheter/tether of the present invention facilitate quick, easy and accurate intraparenchymal positioning of a catheter in the body. Once the catheter is properly positioned it can be used during a diagnostic or therapeutic procedure, either directly or as a passage for other medical devices.

These and other features and advantages will be in part apparent and in part pointed out hereinafter.

BRIEF DESCRIPTION OF THE DRAWINGS

FIG. 1 is a longitudinal cross-sectional view of a first embodiment of a catheter and magnet combination constructed according to the principles of this invention;

FIG. 1A is a longitudinal cross-sectional view of the first embodiment with the magnet partially withdrawn from the distal end of the catheter;

FIG. 2 is a longitudinal cross-sectional view of an alternate construction of the first embodiment of a catheter and magnet combination;

FIG. 3 is a longitudinal cross-sectional view of a second embodiment of a catheter and magnet combination constructed according to the principles of this invention;

Corresponding reference numbers indicate corresponding parts throughout the several views of the drawings.

DETAILED DESCRIPTION OF THE PREFERRED EMBODIMENTS

Figure 4:
FIG. 4 is a top plan view of the magnet and attached tether/guide wire of the second embodiment.

A first embodiment of a catheter and magnet composition constructed according to the principles of this invention is indicated generally as 20 in FIG. 1. The catheter and magnet combination 20 comprises a catheter 22 and a magnet 24. The catheter 22 is of fairly conventional construction, having a proximal end 26, a distal end 28, and a lumen 30 extending therebetween. The catheter 22 can be made of polyurethane tubing, or some other suitable material. The size of the catheter 22 depends upon where in the body it will be introduced, and how it will be used. For use in the brain, the catheter might have an outside diameter of about 3.2 mm and an inside diameter of about 2.8 mm, and a length of about 14 cm.

The magnet 24 is preferably a NdFeB (neodymium-iron-boron) magnet sized to respond to the magnetic field that will be applied to move the catheter and magnet combination through the body. The magnet is sufficiently small to pass through the lumen 30 of the catheter 22. The magnet is preferably elongated so that it can orient the distal tip of the catheter in the presence of an applied magnetic field. A tether 32 extends from the magnet 24 through the lumen 30 of the catheter 22. The tether 32 is preferably made of nitinol, which is highly flexible and resists kinking, although the tether could be made of some other suitable material.

The magnet 24 is preferably positioned inside the lumen 30, adjacent the distal end 28 of the catheter 22. The lumen 30 adjacent the distal end 28 of the catheter 22 preferably has a stricture 34 therein for retaining the magnet 24 in the lumen. In this preferred embodiment, the distal end 28 of the catheter 22 has a tip 36 with a tapering end 38 that forms the stricture 34. The tip 36 may be made of urethane coated tantalum.

With the magnet 24 in the lumen 30 of the catheter 22, the catheter 22 can be introduced into the body and guided to its desired position by the controlled application of magnetic fields. Once the distal end of the catheter 22 has been placed in its desired position, the magnet 24, which is proximal to the stricture 34, can be withdrawn from the lumen 30 by pulling the tether 32 (compare FIG. 1 and FIG. 1a).

As shown in FIGS. 1 and 1a, the magnet 24 has a axial bore therethrough and the tether 32 extends through the bore, terminating in a head 40 that secures the tether to the magnet. An alternative construction of the magnet and tether is shown in FIG. 2. As shown in FIG. 2, the magnet 24' is solid and the tether 32' has a seat 44 on its distal end for engaging the proximal end of the magnet 24'. The magnet 24' can be adhesively held in the seat 44, or the seat can be crimped onto the proximal end of the magnet.

A second embodiment of a catheter and magnet composition constructed according to the principles of this invention is indicated generally as 100 in FIG. 3. The catheter and magnet combination 100 comprises a catheter 102 and a magnet 104. The catheter 102 is of fairly conventional construction, having a proximal end 106, a distal end 108, and a lumen 110 extending therebetween. The catheter 102 can be made of about polyurethane tubing, or some other suitable material. The size of the catheter 102 depends upon where in the body it will be introduced and how it will be used. For use in the brain, the catheter about might have an outside diameter of 3.2 mm and an inside diameter of about 2.8 mm, and a length of about 14 cm.

The magnet 104 is preferably a NdFeB (neodymium-iron-boron) magnet sized to respond to the magnetic field that will be applied to orient the catheter and magnet combination inside the body. The magnet 104 is sufficiently small to pass through the lumen 110 of the catheter 102. The magnet preferably has an elongate shape to allow the magnet to be oriented in an applied magnetic field. In this preferred embodiment, the magnet is a cylinder about 2.2 mm inches in diameter and about 0.6 cm long. The magnet may be encapsulated in a urethane coating.

Figure 5:
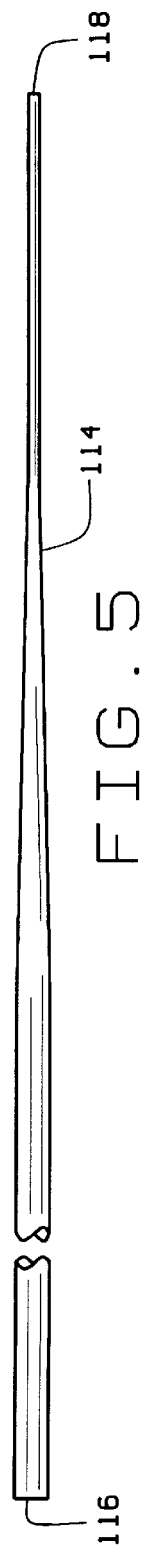
FIG. 5 is a top plan view of guide wire core of the tether/guide wire shown in FIG. 4.

A tether 112 extends from the magnet 104 through the lumen 110 of the catheter 102. In the preferred embodiment, the overall length of the tether is about 51.2 inches (130 cm). The tether comprises a core guide wire 114, which is preferably made of nitinol. The guide wire 114 has a proximal end 116 and a distal end 118 (see FIG. 5). As shown in FIG. 5, the guide wire 114 tapers toward the distal end 118, so that the distal end of the guide wire is more flexible than the proximal end. In this preferred embodiment the guide wire 114 has a diameter of 0.033 inches (0.084 cm) and tapers over the distal 3.9 inches (10 cm) to a diameter of about 0.011 inches (0.028 cm).

The distal end 118 of the guide wire 114 extends through an axial bore 120 in the magnet 104. A cap of epoxy 122 secures the magnet 104 to the guide wire 114.

Figure 6:
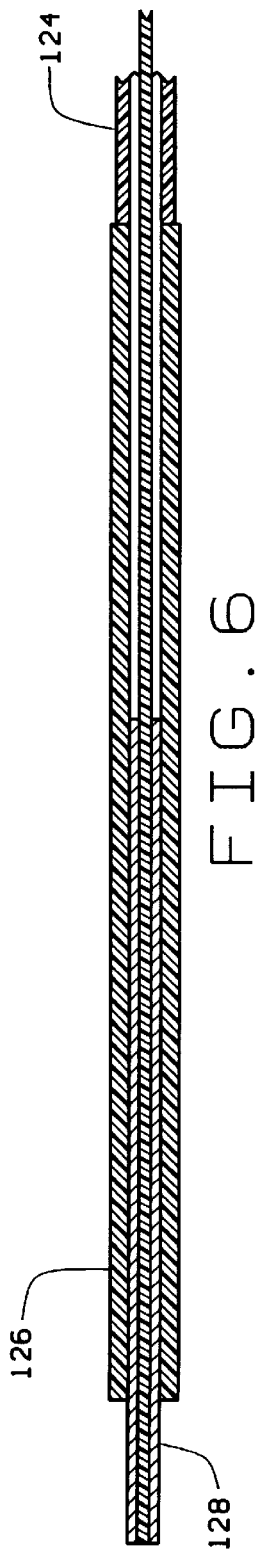
FIG. 6 is a vertical longitudinal partial cross-sectional view of the distal end of the tether/guide wire taken along the plane of line 6—6 in FIG. 4.
Figure 7:
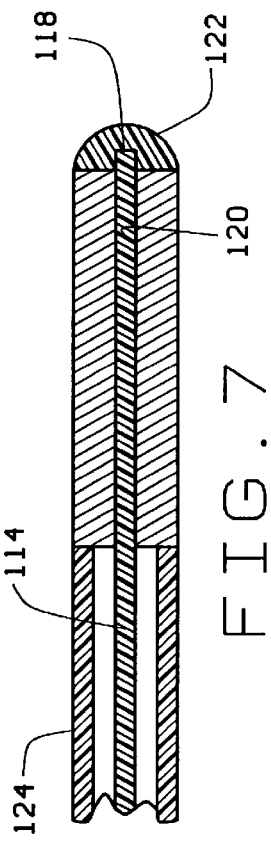
FIG. 7 is a vertical, longitudinal partial cross-sectional view of the proximal end of the tether/guide wire taken along the plane of line 7—7 in FIG. 4.

The distal portion of the guide wire 114 is covered with a sheath 124, made of flexible polyurethane tubing. The sheath 124 preferably has the same outside diameter as the magnet 104, to smoothly slide in the lumen 110, and to help prevent the excessive movement of the tether within the lumen. In this preferred embodiment the sheath 124 is about 36 inches (91 cm) long. The sheath 124 is preferably secured to the proximal end of the magnet 104 with an adhesive, such as SICOMET 40 FDA approved epoxy, available from Tracon. The proximal portion of the guide wire is covered with a sheath 126 made of braided polyethylene tubing. In this preferred embodiment, the sheath 126 is about 13.5 inches (34.3 cm) long. A metal cannula 128 (see FIG. 6) covers the proximal portion of the wire, and extends partly under the sheath 128. In this preferred embodiment, the cannula 128 extends proximally of the sheath 126 about 1.1 inches (2.8 cm). The sheath 126 and the metal cannula 128 help stiffen the proximal portion of the tether 112 so that the tether can be used to push the catheter, into which it is inserted, through the tissues of the body.

The magnet 104 is preferably positioned inside the lumen 110, adjacent the distal end 108 of the catheter 102. The lumen 110 adjacent the distal end 108 of the catheter 102 preferably has a stricture 130 therein for retaining the magnet 104 in the lumen. In this preferred embodiment, the distal end 108 of the catheter 102 has a tip 132 with a tapering end 134 that forms the stricture 130. The tip 132 may be made of urethane coated tantalum.

With the magnet 104 in the lumen 110 of the catheter 102, and the tether 112 extending through the lumen and out the distal end, the catheter 102 can be introduced into the body. The distal end of the tether 112 is highly flexible, and thus the magnet 104 inside the lumen can be oriented by the controlled application of magnetic fields, so that the distal end of the catheter 102 can be pointed in a particular direction. Once the distal end 108 of the catheter 102 is pointing in the desired direction, the catheter can be advanced in that direction by pushing the proximal end of the tether 112, which pushes the catheter. The distal end 108 of the catheter 102 can be reoriented, by changing the magnetic field to reorient the magnet 104, and the catheter advanced by pushing on the proximal end of the tether 112.

Once the distal end 108 of the catheter 22 has been placed in its desired position, the magnet 104, which is proximal to the stricture, can be withdrawn from the lumen 110 by pulling the tether 112. The catheter 102 can than be used directly for a diagnostic or therapeutic medical procedure, or the catheter can be used as a passageway for other medical devices to perform a diagnostic or therapeutic medical procedure.

Operation

In operation, the catheter and magnet combination 20 is introduced through an opening in the body. A magnetic field is applied to orient and advance the catheter and magnet combination through the tissue to the desired position. Once the distal end 28 of the catheter is in its desired position, the magnet 24 is removed from the catheter 22 by pulling the tether 32 to withdraw the magnet through the lumen 30 of the catheter.

In operation, the catheter and magnet combination 100 is introduced through an opening in the body. A magnetic field is applied to orient the magnet 104 in the distal end 108 of the catheter 102, and the catheter is advanced in the direction that the tip is pointing by pushing the tether 112. Once the distal end 28 of the catheter is in its desired position, the magnet 104 is removed from the catheter 102 by pulling the tether 112 to withdraw the magnet though the lumen 110 of the catheter.

Once the catheter 22 or 102 is in position it can be used to perform a medical procedure or it can be used as a guide to insert medical devices to the area surrounding the distal end of the catheter to perform a medical procedure.

What is claimed:

1. In combination with a catheter having a proximal and distal end and a lumen therebetween, a magnet in the distal end of the lumen so that the distal end of the catheter can be positioned within the body with the aid of an externally applied magnetic field, and a tether attached to the magnet and extending through the lumen and out the proximal end so that the magnet can be removed from the catheter through the lumen once the distal end of the catheter is properly positioned.

2. The combination according to claim 1 wherein the distal end of the lumen has a stricture for preventing the magnet from exiting through the distal end of the catheter.

3. A method of positioning the distal end of a catheter within the body, the method comprising:

placing a magnet inside the lumen of the catheter adjacent the distal end, the magnet having a tether extending through the lumen and out the proximal end;

inserting the distal end of the catheter into the body;

applying a magnetic field to the distal end of the catheter to help guide the distal end of the catheter to the desired position within the body;

pulling the tether to withdraw the magnet from the lumen of the catheter once the distal end of the catheter is properly positioned.

4. A method of positioning the distal end of a catheter within the body, the method comprising:

inserting a guide wire having a magnet on its distal end into the lumen of the catheter until the magnet is adjacent the distal end of the catheter;

inserting the catheter into the body;

moving the distal end of the catheter to the desired position within the body by applying a magnetic field to the magnet in the distal end of the catheter to orient the distal end of the catheter in the desired direction of travel, and advancing the catheter in the desired direction by advancing the guide wire.

5. A method of positioning the distal end of a catheter within the body, the method comprising the step of inserting into the body the distal end of a catheter, having a guide wire with a magnet on its distal end in the lumen with the magnet adjacent the distal end, and moving the distal end of the catheter to the desired position within the body by applying a magnetic field to the magnet in the distal end of the catheter to orient the distal end of the catheter in the desired direction of travel, and advancing the catheter in the desired direction by advancing the guide wire.

6. A method of positioning the distal end of a catheter within the body, the method comprising the step of inserting into the body the distal end of a catheter having a magnet in the lumen adjacent the distal end; moving the distal end of the catheter to its desired position in the body by applying a magnetic field to the magnet in the catheter, and removing the magnet through the lumen of the catheter.

7. A method of positioning the distal end of a catheter within the body, the method comprising the step of inserting into the body the distal end of a catheter having a magnet in the lumen adjacent the distal end; moving the distal end of the catheter to its desired position in the body by applying a magnetic field to the magnet in the catheter to orient the distal end of the catheter; and advancing the catheter with a guide wire extending through the lumen of the catheter.

8. A guide wire adapted to be inserted into the lumen of a catheter to position the distal end of the catheter within the body, the guide wire having a proximal end and a distal end, the guide wire being more flexible adjacent the distal end than the proximal end, and a magnet on the distal end so that when the guide wire is in the lumen of a catheter, the magnet is adjacent the distal end of the catheter, the distal portion of the guide wire being sufficiently flexible to allow the magnet to move in response to a magnetic field to orient the distal tip of the catheter, and the proximal portion of the guide wire being sufficiently stiff to allow the guide wire to push the catheter through the body.

9. A catheter for being magnetically guided as it is advanced through an opening in a patient's body, said catheter comprising a magnetic tip positioned near a distal end of the catheter, and a tether attached to the magnet to permit withdrawal of the magnetic tip after the catheter has been desirably positioned.

10. The catheter of claim 9 wherein the magnetic tip is slidably received with the catheter and wherein the catheter has a structure preventing the magnetic tip from being driven out of the distal end of the catheter.

11. The catheter of claim 10 wherein the tether comprises a wire extending through the catheter and attached to the magnetic tip.

12. The catheter of claim 11 wherein the catheter comprises a lumen, and wherein the magnetic tip is sized to slide within the lumen, and wherein the structure comprises a taper at the distal end of the lumen to thereby physically prohibit the exit of the magnetic tip out of the distal end.

13. The catheter of claim 12 wherein the magnetic tip further includes an axial bore through which the tether extends and the tether further comprises a head secured to its distal end and which has a radial dimension large enough to prevent its being drawn throughout the axial bore so that as the head is positioned distal to the magnetic tip, the head contacts it to pull it out of the catheter as the tether is withdrawn therefrom.

14. The catheter of claim 13 further comprises a sheath surrounding the tether and having approximately the same cross section as the magnetic tip so that both the magnetic tip and the tether slide smoothly within the catheter.

15. The catheter of claim 14 further comprising a second sheath and rigid cannula surrounding a proximal end of the tether, the second sheath abutting the first sheath and the rigid cannula being positioned within the second sheath.

16. The catheter of claim 12 wherein the tether further comprises a seat on its distal end for engaging the proximal end of the magnetic tip and for being attached thereto.

17. The catheter of claim 16 further comprising a sheath surrounding the tether and having approximately the same cross section as the magnetic tip so that both the magnetic tip and the tether slide smoothly within the catheter.

18. The catheter of claim 17 further comprising a second sheath and rigid cannula surrounding a proximal end of the tether, the second sheath abutting the first sheath and the rigid cannula being positioned within the second sheath.

* * * * *